United States Patent [19]

Buckberg

[11] Patent Number: 4,988,515
[45] Date of Patent: Jan. 29, 1991

[54] CARDIOPLEGIC SOLUTION

[75] Inventor: Gerald D. Buckberg, Los Angeles, Calif.

[73] Assignee: The Regents of the Univ. of Calif., Berkley, Calif.

[21] Appl. No.: 333,789

[22] Filed: Apr. 5, 1989

Related U.S. Application Data

[63] Continuation of Ser. No. 148,151, Jan. 28, 1988, abandoned, which is a continuation of Ser. No. 768,404, Aug. 21, 1985, abandoned.

[51] Int. Cl.$^5$ .................. A61K 35/14; A61K 31/70; A61K 31/195
[52] U.S. Cl. ................................ 424/529; 424/682; 514/23; 514/561
[58] Field of Search ............... 514/561, 23; 424/101, 424/682, 529

[56] References Cited

U.S. PATENT DOCUMENTS

| | | | |
|---|---|---|---|
| 4,249,923 | 2/1981 | Walda | 62/394 |
| 4,254,081 | 3/1981 | Streczyn et al. | 422/46 |
| 4,314,550 | 2/1982 | Apstein | 128/1 |
| 4,415,556 | 11/1983 | Bretschneider | 424/153 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |

OTHER PUBLICATIONS

Bretschneider, H. J., Hobner, G., Knoll, D., Lohr, B., Nordbeck II, and Spieckermann, P. G., Myocardial resistance and tolerance to ischemia: Physiological and biochemical basis, J. Cardiovasc Surg 16, 241–260, 1975.

Schulte, H. G., Preusse, C. J., Groschopp, C., Bircks, W., and Bretschneider solution, Textbook of Clinical cardioplegia, Eds Engelman & Levitsky, pp. 199–210, 1982.

Follette, D. M., Mulder, D. G., Maloney, J. V., Buckberg, G. D., Advantages of blood cardioplegia over continuous coronary perfusion or intermittent ischemia, J. Thor and Cardiovasc Surg 76(5), 604–619, 1978.

Lavallee, M., Cox, D., Patrick, T. A., Vatner, S. F., Salvage of myocardial function by coronary artery reperfusion 1, 2 and 3 hours after occlusion in conscious dogs, Circulation Research 53(2), 235–247, 1983.

Jennings, R. B., Reimber, K. A., Factors involved in salvaging ischemic myocardium: effect of reperfusion of arterial blood, Circ 68:I, 25–36, 1983.

Selinger, S. L., Berg, R., Leonard, J. J., Coleman, W. S., DeWood, M. A., Surgical intervention in acute myocardial infarction, Tx Hrt Inst J 11, 1:44–51, 1984.

Follette, D. M., Fey, K., Buckberg, G. D., Helly, J. J., Steed, D. L., Foglia, R. P., Maloney, J. V., Reducing postischemic damage by temporary modification of reperfusate calcium, potassium, pH, and osmolarity, J. Thor and Cardiovasc Surg 82(2), 221–238, 1981.

Rosenkranz, E. R., Buckberg, G. D., Myocardial protection during surgical coronary reperfusion, J Am Coll Cardiol 1(5), 1235–1246, 1983.

Rosenkranz, E. R., Buckberg, G. D., Laks, H., Mulder, D. G., Warm induction of cardioplegia with glutamate-enriched blood in coronary patients with cardiogenic shock who are dependent on inotropic drugs and intraaortic balloon support, J of Thor and Cardiovasc Surgery, vol. 86, No. 4, pp. 507–518, Oct. 1983.

Rosenkrantz, E., Medical Research Abstract Reproduction Form from American Heart Association, Oct. 1983.

(List continued on next page.)

Primary Examiner—Jacqueline Stone
Attorney, Agent, or Firm—Poms, Smith, Lande & Rose

[57] ABSTRACT

An improved amino acid enriched cardioplegic solution adapted for use in preventing and treating heart muscle damage due to regional ischemia. The solution includes a calcium ion concentration of between about 50–300 umol, a metabolizable substrate concentration of 400–1000 mg % and an osmolarity of between about 400–500 mOsmols.

18 Claims, 5 Drawing Sheets

OTHER PUBLICATIONS

Kugelmeier, J. et al., Clinical Evaluation of Three Methods of Myocardial Protection, pp. 436–443.

Lazar, H. L., Buckberg, G. D., Manganaro, A. M., Becker, H., Myocardial energy replenishment and reversal of ischemic damage by substrate enhancement of secondary blood cardioplegia with amino acids during reperfusion, J. Thor Cardiovasc Surg 80, 350–359, 1980.

Buckberg, G. D., A Proposed "Solution" to the Cardioplegic Controversey, J. Thor Cardiovasc Surg, vol. 77, No. 6, pp. 803–815, Jun. 1979.

The Lancet, Feb. 22, 1986, G1551, pp. 397–401.

J. Thoracic and Cardiovascular Surgery, vol. 92, No. 3, Part 2 Supplement.

The Merck Index "Succinic Acid", No. 8743, p. 1271, 10th Ed. 1983.

Irisawa et al. cited in Biological Abstracts 77(10):8073, Ref. 73310, 1984.

Koomen et al., cited in Chem. Abstracts, vol. 99, No. 860424, 1983.

(GLUCOSE CONCENTRATION GREATER THAN 400 MG %)

CARDIOPLEGIC SOLUTION

This is a continuation of co-pending application Ser. No. 07/148,151 filed on Jan. 28, 1988, which is a continuation of Ser. No. 06/768,404, filed Aug. 21, 1985, both now abandoned.

BACKGROUND OF THE INVENTION

The present invention relates generally to solutions which are used in treating the heart. More particularly, the present invention relates to an improved amino acid enriched cardioplegic solution which is designed for use as a solution to be infused directly into the heart in order to either protect the heart against ischemic damage when its blood supply is interrupted (i.e., during routine open heart surgery) or to avoid or reverse ischemic damage to the heart which has been deprived of its blood supply (i.e., acute coronary occlusion) while such blood supply is re-established under controlled conditions (i.e., in the operating room or in the cardiac catheterization laboratory).

This invention was made with Government support under Grant No. HL 16292 awarded by the National Institutes of Health. The Government has certain rights in this invention. The publications and other reference materials referred to herein to describe the background of the invention and to provide additional detail regarding its practice are hereby incorporated by reference. For convenience, the reference materials are numerically referenced and grouped in the Bibliography at the end of the Detailed Description of the Invention.

Cardioplegic solutions are chemical solutions designed to stop the heart and reduce its energy demands during cardiac surgery. They are used by most surgeons worldwide to protect the heart from damage when its blood supply must be interrupted while the cardiac condition is corrected surgically (1,2).

Several years ago, the concept of using oxygenated blood as the vehicle to deliver the cardioplegic solution was introduced (3). This "blood cardioplegia" is usually prepared by first formulating an aqueous solution of concentrated ingredients. The concentrated solution is then diluted with blood and introduced into the heart. This concept of blood cardioplegia was developed from studies of "reperfusion damage" whereby the heart which is deprived of blood supply can be shown to be intact structurally while its blood supply is interrupted, but undergoes dramatic deleterious changes when blood supply is re-established with normal unmodified blood.

Experimental studies have shown that recovery of muscle function can be delayed for up to a month when revascularization occurs after two hours (4) and further, that six hours of coronary flow interruption provides irreversible damage (5). Clinical studies have confirmed that reperfusion with normal blood either in the catheterization laboratory or in the operating room fails to provide immediate recovery of muscle function during hospitalization. Follow-up studies after one year show that revascularization after 6 hours does not restore contractility (6).

Early studies have shown that delivering an initial reperfusate of warm blood with low calcium, alkalosis, and high potassium avoids the above-described damage (7). Subsequent studies have demonstrated that enrichment of the cardioplegic solution with the amino acid glutamate (8,9) and more recently aspartate (10) improve markedly the recovery obtained after cardiac operations in hearts which must undergo operation after they have been damaged acutely.

The amino acid enriched cardioplegic solutions presently in use are made by diluting a previously prepared concentrated aqueous solution with blood or some other diluent containing a source of oxygen to form a cardioplegic solution for intraoperative utilization which includes: an ionic calcium concentration of above 500 umol; a concentration of glucose or other metabolizable substrate of below 400 mg %; a pH of 7.7–7.8; and an osmolarity of below 400 mOsmol.

Although the above described amino acid enriched cardioplegic solutions have markedly improved cardiac recovery, there is still a continuing need to provide even more effective cardioplegic solutions. In addition, it would be desireable to provide cardioplegic solutions which not only prevent heart muscle damage due to ischemia, but also are effective in reversing such damage

SUMMARY OF THE INVENTION

In accordance with the present invention, an improved amino acid enriched cardioplegic solution is disclosed which prevents heart muscle damage and provides increased cardiac recovery from damage to ischemia. In addition, cardioplegic solutions in accordance with the present invention are useful in treating hearts to reduce damage already present due to ischemia.

The present invention is based upon an improved amino acid enriched cardioplegic solution which is adapted for use in treating the heart to prevent or reverse heart muscle damage due to regional ischemia (i.e., acute coronary occlusion). The improvement involves maintaining the calcium ion concentration of the cardioplegic solution between about 100–300 umol while maintaining the concentration of glucose or other metabolizable substrate between about 400–1000 mg % and maintaining the osmolarity of the solution between about 400–500 mOsmol. It was surprisingly discovered that the effectiveness of amino acid enriched cardioplegic solutions increased dramatically when the calcium ion concentration, metabolizable substrate concentration and osmolarity of the solution are in the above described ranges.

In addition to providing increased effectiveness as a cardioplegic solution for preventing cardiac damage during surgery, the cardioplegic solution in accordance with the present invention was also surprisingly found to be effective in reducing damage and increasing recovery in cardiac muscles having preexisting damage due to ischemia.

The above-discussed and many other features and attendant advantages of the present invention will become apparent as the invention becomes better understood by reference to the following detailed when considered in conjunction with the accompanying drawings.

DETAILED DESCRIPTION OF THE INVENTION

Figure 1:
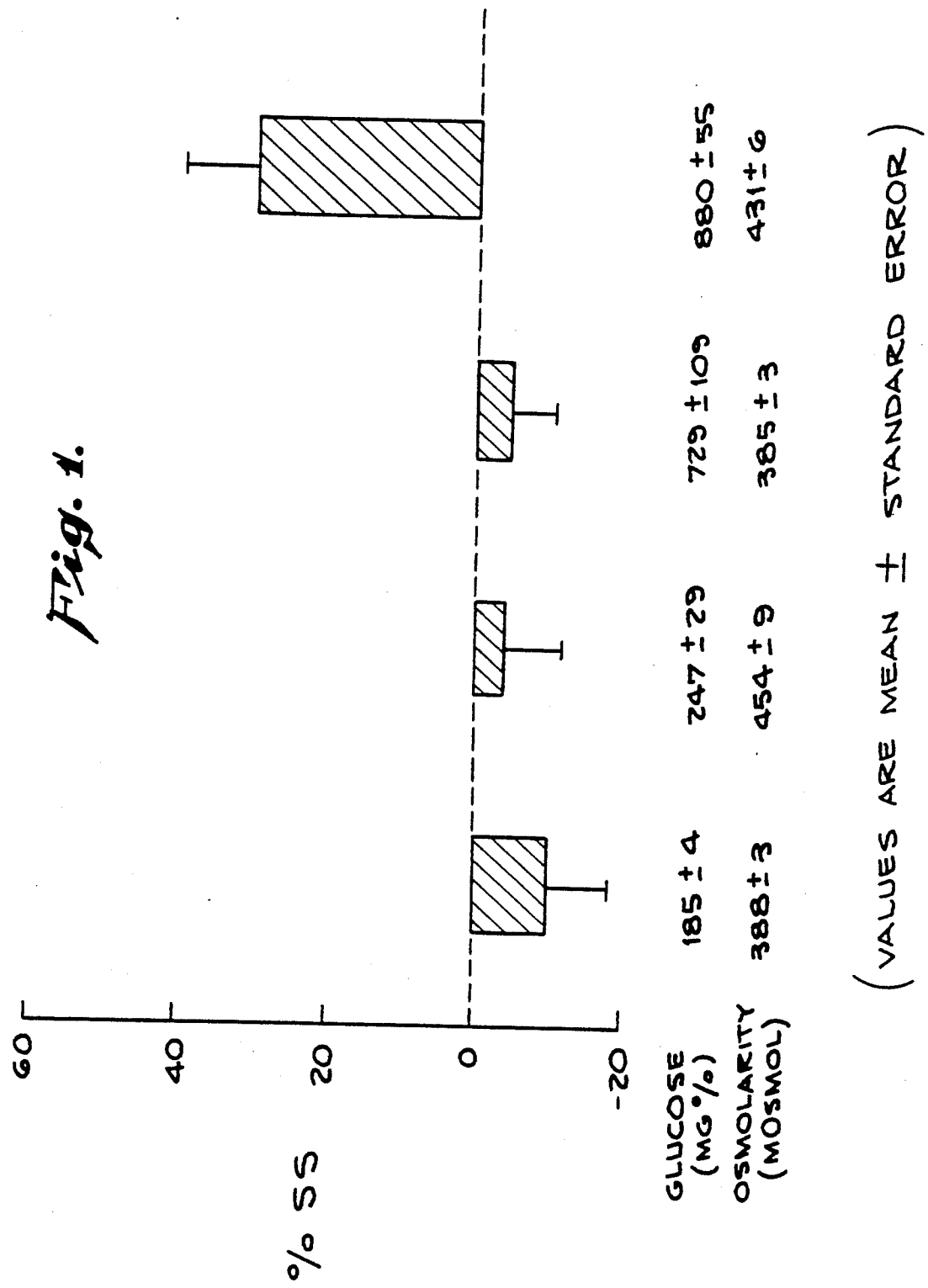
FIG. 1 is a graph representing test results which demonstrate the increased percent systolic shortening due to the use of reperfusate having hyperosmolarity (mOsmol greater than 400) and hyperglycemia (glucose greater than 400 mg %) in accordance with the present invention.

The present invention is an improvement upon amino acid enriched cardioplegic solutions of the type disclosed in reference Nos. 9 and 10. These solutions are blood cardioplegia in which various ingredients are added in order to regulate the ionic calcium concentration, glucose concentration, osmolarity, pH, and potassium concentration. The actual cardioplegic solution (blood cardioplegia) which is introduced into the heart can be prepared by mixing various additives such as Tromethamine solution (THAM), Citrate-Phosphate-Dextrose solution (CPD), Dextrose, and Potassium Chloride, directly into the blood. More preferably, a concentrated aqueous solution of the various additives is prepared. This concentrated aqueous solution is then diluted with blood to provide a blood cardioplegic solution having the desired pH, osmolarity, and concentrations of calcium ion, amino acids, and glucose. Blood is the preferred diluent or carrier; however, other cardioplegia compatible diluents, such as stroma free hemaglobin, oxygenated plasma, crystalloids and fluorocarbons, may be used so long as a suitable source of oxygen is provided by the diluent. Other assanguineous or accellular carriers which are capable of becoming oxygenated may be used.

CPD solution is available from Sorenson Research Company Division of Fenwal Laboratories in 500 ml bottles having the following composition for each 100 ml 2.63 gms sodium citrate (hydrous USP)
2.55 gms dextrose (hydrous USP)
327 mgm citric acid (hydrous USP)
222 mgm sodium biphosphate USP THAM solution is available from Abbott Laboratories in 500 ml bottles of 0.3 molar solution having the following composition for each 100 ml:

Tromethamine 3.6 gms
pH adjusted with acetic acid (approx. 8.4 mEq/100 ml)
9.3 molar solution
approximate pH 8.6
380 mOsm/liter (calculated)

A preferred blood cardioplegia in accordance with the present invention will have a pH of 7.5–7.7, an osmolarity of 400–500 mOsmol, and an aspartate concentration of 10–30 mmol, a glutamate concentration of 10–30 mmol, a metabolizable substrate concentration of 400–1000 mg % and calcium ion concentration of 150–300 umol. Although glucose is the preferred metabolizable substrate for use in accordance with the present invention, other metabolizable substrates such as fructose, malate, succinate and pyruvate may be used in place of glucose. Equal molar amounts of glutamate and aspartate are also preferred. However, cardioplegia enriched with other suitable amino acids, such as arginine or ornithine, may be used if desired.

The concentration of potassium chloride in the blood cardioplegia will be varied, as is well known, depending upon whether the solution is being used to stop heart function, maintain heart function after heart stoppage or treatment of a previously ischemia damaged heart.

As mentioned above, it is preferred to prepare the blood cardioplegia by mixing blood with a concentrated aqueous solution to provide a final blood cardioplegic solution having the desired above-mentioned ultimate concentrations. Preferably the blood:concentrated solution ratio will be about 4:1. An exemplary concentrated solution is made by mixing the following solutions in the quantities listed to form one liter of solution.

| Ingredient | Quantity |
| --- | --- |
| Citrate Phosphate Dextrose (CPD) | 200 to 250 ml |
| Tromethamine (THAM) (0.3 M) | 200 to 250 ml |
| Aspartate/Glutamate Solution (0.23 mol Glutamate, 0.23 mol Aspartate) | 200 to 300 ml |
| Glucose (DSW-5% dextrose in 0.2 N saline) | 200 to 300 ml |
| Glucose (D50W-50% dextrose in 0.2 N Saline) | 30 to 50 ml |
| KCl (2 mEq/ml) | 10 to 30 ml |

The concentrated aqueous solution can also be made by mixing the following ingredients with distilled water (USP) to form a liter of concentrated solution:

| | |
| --- | --- |
| Monosodium Glutamate Monohydrate | 9.0–13.0 gm. |
| Monosodium Aspartate Monohydrate | 8.0–12.0 gm. |
| Citric Acid Monohydrate | 0.5–1.1 gm. |
| Sodium Citrate Dihyate | 5.0–8.0 gm. |
| Sodium Phosphate Monobasic Monohydrate | 0.3–1.0 gm. |
| Dextrose, Anhydrous | 30.0–40.0 gm. |
| Tromethamine | 7.0–12.0 gm. |
| Potassium Chloride | 1.0–5.0 gm. |
| Water for injection USP | 1000 ml (qs) |

KCl is added to the above solution in amounts ranging from 1.0 to 5.0 gms depending upon whether the solution will be used to stop the heart, maintain the heart after stoppage or treat a heart that is suffering from prior ischemic damage.

An exemplary preferred concentrated solution is as follows:

| | |
| --- | --- |
| Mosodium Glutamate Monohydrate | 10.7 gm |
| Monosodium Aspartate Monohydrate | 9.8 gm |
| Citric Acid Monohydrate | 0.8 gm |
| Sodium Citrate Dihydrate | 6.6 gm |
| Sodium Phosphate Monobasic Monohydrate | 0.55 gm |
| Dextrose, Anhydrous | 35.30 gm |
| Potassium Chloride | 2.24 gm |
| Tromethamine | 9.1 gm |
| Water for injection USP | 1000 ml (qs) |

The concentrated aqueous solutions in accordance with the present invention are used in the same well known manner as other concentrated solutions which are mixed with blood or other diluent to provide a cardioplegic solution.

Figure 5:
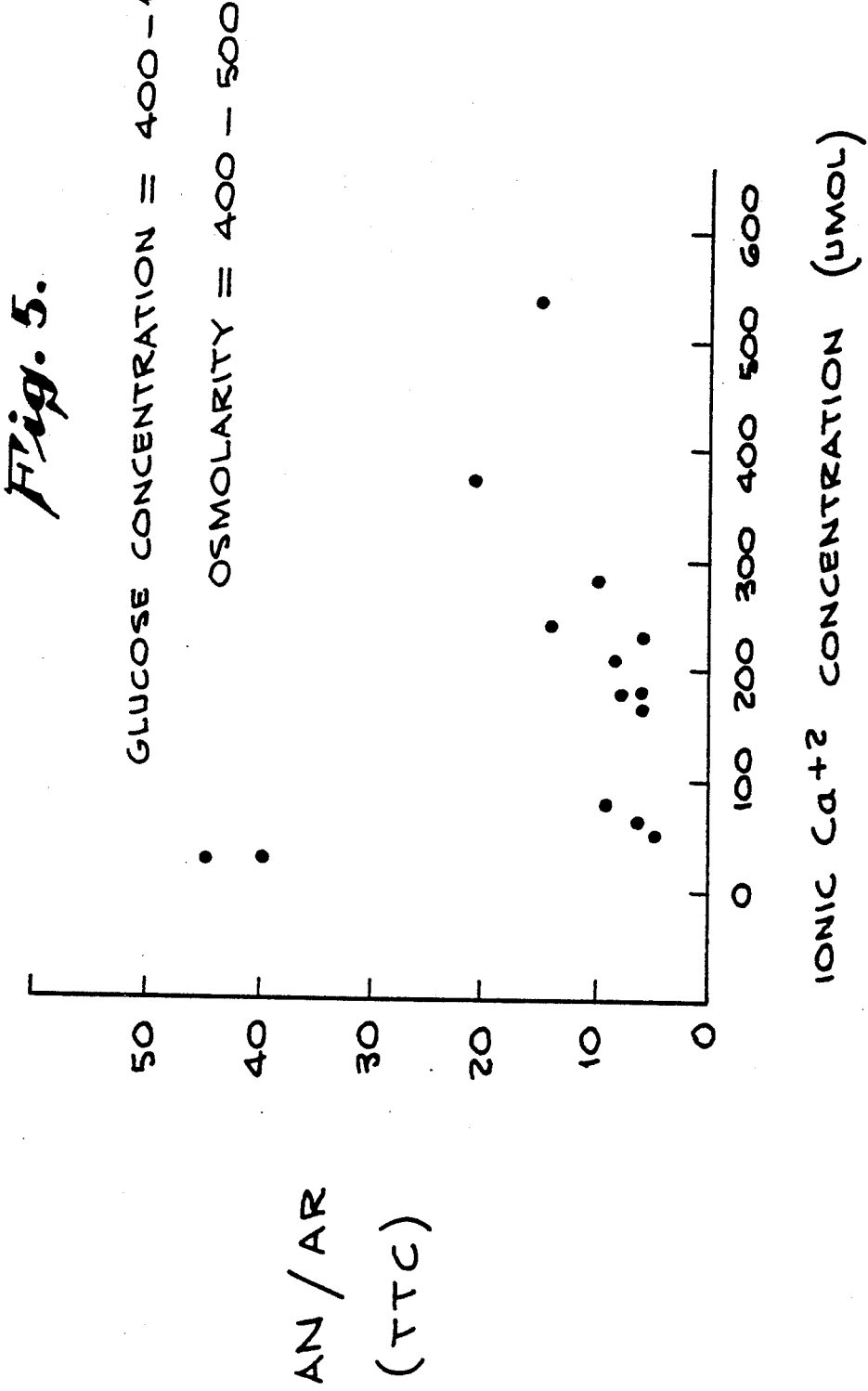
FIG. 5 is a graph representing test results which demonstrate that the salvage of damaged myocardial muscle is most consistent when the ionic calcium concentration of the reperfusate is between about 50–300 mol.

The term "Blood cardioplegic solution" as used herein is not strictly limited to solutions for use in stopping the heart and maintaining a low level of heart activity during open heart surgery. The cardioplegic solution, in accordance with the present invention, may also be used as a resuscitative fluid for reperfusion of patients with acute myocardial infarction. As shown in FIG. 5, blood cardioplegia in accordance with the present invention provides salvage of heart muscle previously damaged with regional ischemia. Accordingly, applicant's use of the term "cardioplegic solutions" is not intended to limit the use of applicant's improved composition to cardioplegia only.

Various drugs having known activity can be added to the basic cardioplegia formulations set forth above. For example, steroids, such as methyl prednisolone and prednisolone, may be added to the cardioplegic solution in order to limit membrane damage. Both of the compounds are available from Upjohn Laboratories (Kalamazoo, Mich.). Oxygen radical scavengers such as co-enzyme $Q_{10}$, Allopurinal, superoxide dismutase and catalase may also be added. Co-enzyme $Q_{10}$ is available from Eisai Co., Ltd. (Tokyo, Japan). Other oxygen radical scavengers such as Allopurinol (Schein Laboratories—Pt. Washington, N.Y.), Superoxide Dimutase (Sigma—St. Louis, Mo.) and Catalase (Sigma—St. Louis, Mo.) may also be used. Various calcium channel blockers such as Diltiazem and Verapamil may also be introduced. Diltiazem is available from Eli Lily Laboriatories (Indianapolis, Ind.) and Verapamil is available from Knoll Laboratories (Whippany, N.J.). Adenine nucleotide precursors such as AICAR and ribose may also be added. AICAR and Ribose are both available from Sigma (St. Louis, Mo.).

The preferred doses for the above-additional additives are set forth as follows:

| | |
|---|---|
| Prednisdone/Methyl Prednisdone | 10–30 mg/Kg body weight |
| Coenzyme Q10 | 400 mg/L |
| Diltiazem | 300 mg/Kg body weight |
| Verapamil | 1–4 mg/Kg body weight |
| Ribose | 250 mg/L |
| AICAR | 10 mMol |

In order to fully illustrate the invention, examples of practice are set forth below.

FIGS. 1–5 are graphic representations of the results of a series of tests done on dogs in which blood cardioplegic solutions with the same basic formula, but having varying osmolarity, the glucose concentration and calcium ion concentration were administered as the initial reperfusate after 2 hrs. of acute coronary occlusion.

The cardioplegic solution was prepared by initially preparing an aqueous concentrated solution and then diluting this solution 1 to 4 with blood. The basic ingredients used to formulate one liter batches of the concentrated solutions were: Monosodium Glutamate Monohydrate, Monosodium Aspartate Monohydrate, Citric Acid Monohydrate, Sodium Citrate Dihydrate, Sodium Phosphate Monobasic Monohydrate, Dextrose, (Anhydrous), Tromethamine, Potassium Chloride and Water USP (gs to 1000 ml).

These ingredients were varied to give the various glucose concentrations, calcium ion concentrations and osmolarities represented in the figures. The glutamate and aspartate concentrations were the same for all tests (10.69 monosodium glutamate monohydrate and 9.81 gm monosodium aspartate monohydrate) The pH of the blood cardioplegia solutions were maintained between 7.5–7.7. The solutions were tested on dogs following the experimental model set forth below.

All dogs were anesthetized with sodium thiamylal (30 mg/kg iv) and maintained with sodium pentobarbital (30 mg/kg) and breathed by positive pressure endotracheal ventilation with 100% oxygen. The chest was opened by median sternotomy, the pericardium incised and cradled, and the left anterior descending coronary artery dissected adjacent to its first diagonal branch for subsequent occlusion to produce an area of risk of approximately 30%. Ultrasonic dimension crystals (2–2.5 mm in diameter) were inserted subendocardially parallel to the direction of the merdional fibers, in the center of the eventual ischemic zone. Instantaneous segmental length was determined by sonomicrometer (Triton Technology, Inc., San Diego, Calif.). Catheters were placed into the aortic arch via the internal mammary artery, left atrium and into the left ventricular cavity for measuring pressure and for timing the cardiac cycle to synchronize with segmental crystal recordings.

All dogs were given heparin (3 mg/kg) and underwent cannulation of the femoral artery and right atrium via the femoral vein (#30 French cannula). Preparations for left ventricular venting were made by advancing a 12 French multi-holed cannula across the aortic valve and into the left ventricle via the carotid artery. These cannulae were connected to a pump oxygenator circuit primed with 1500 ml whole blood and 300 ml Hespan (hydroxy ethyl starch in 0.9% NaCl solution). The extracorporeal circuit was used temporarily during the ischemic period to facilitate defibrillation and thereby increase the yield of experiments which could be completed.

A 1.2 French O.D. catheter was placed into the left anterior descending artery beyond the potential occlusive site in each of the dogs selected to undergo regional cardioplegic reperfusion. A lidocaine injection (2 mg/kg) was given immediately before occlusion and a lidocaine infusion (1 mg/min) was given throughout the period of ischemia and reperfusion. Reperfusion utilizing the blood cardioplegia was carried out according to the method set forth in Reference 9.

All hemodynamic and functional data were recorded on a Honeywell 1612 Visicorder Oscillograph. Anterior segmental systolic shortening (ss) was calculated as:

$$ss = 100 \times \frac{EDL - ESL}{EDL}$$

where EDL and ESL are end diastolic length and end systolic length respectively. Myocardial contractile reserve capacity was tested by eliciting by postextrasystolic beats and calcium chloride injection (10 mg/kg). Results were expressed as percent of systolic shortening relative to control values to allow comparison between dogs and avoid bias relative to differences in heart size and distance between crystals.

The percent systolic shortening relative to the control (% SS) is a standard measure of the effectiveness of a cardioplegic solution. The more positive the recovery of % SS is, the more effective the cardioplegic solution has been in avoiding reperfusion damage. Negative % SS indicate an ineffective cardioplegic solution.

Figure 2:
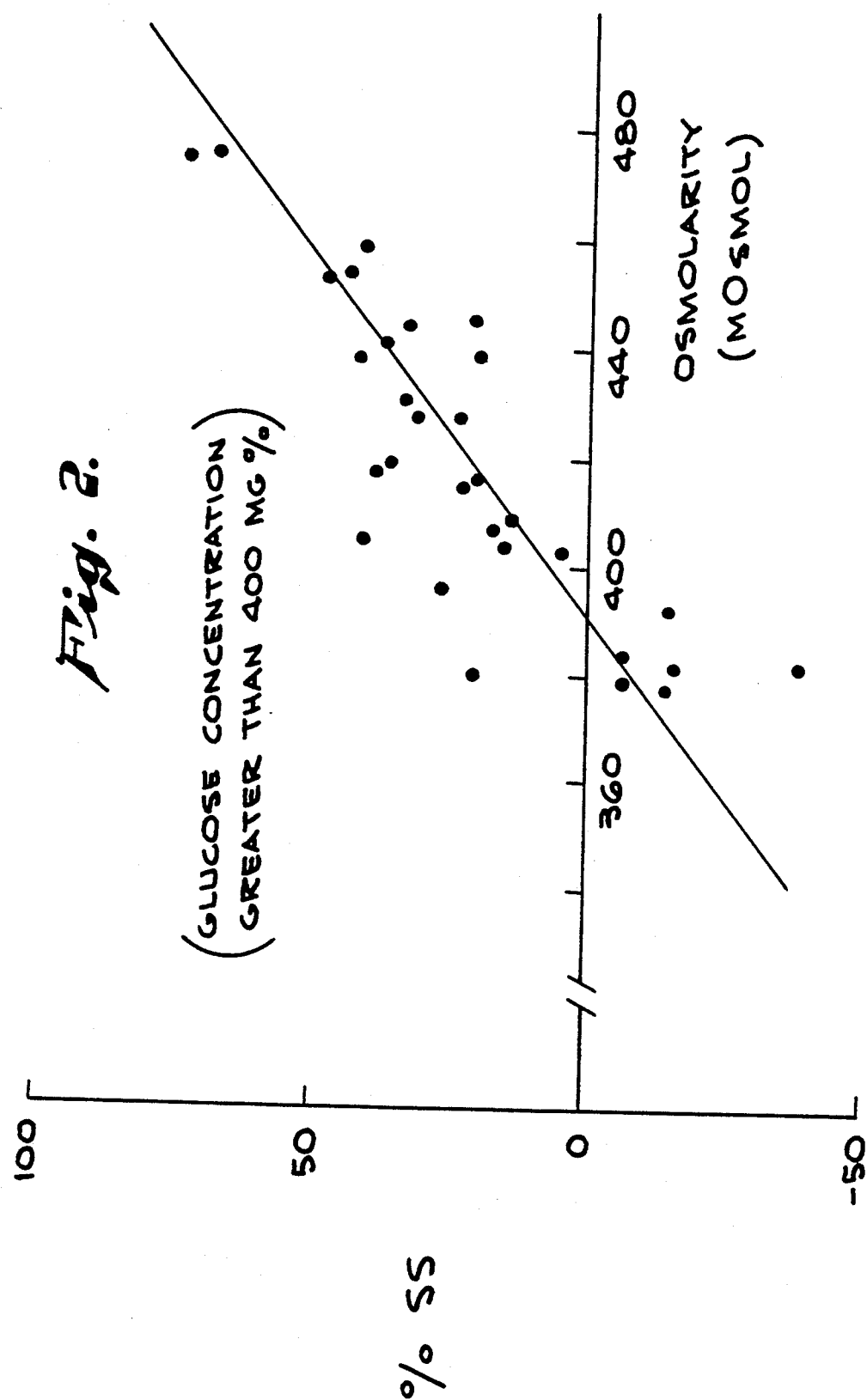
FIG. 2 is a graph representing test results which show that consistent spontaneous systolic shortening is achieved only when both the amount of glucose in the reperfusate is over 400 mg % and the osmolarity is greater 400 mOsmol.
Figure 3:
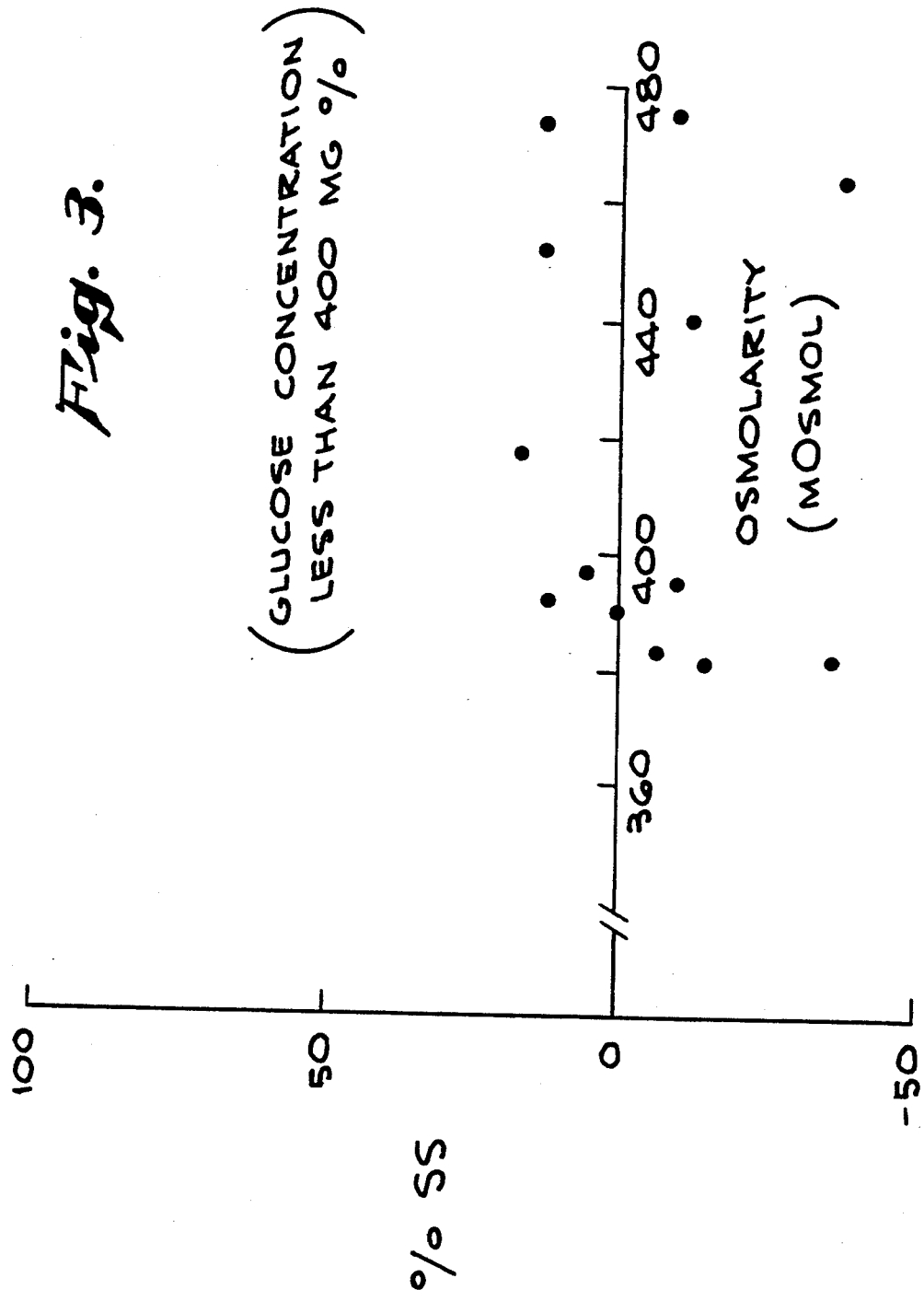
FIG. 3 is a graph representing test results which demonstrate that consistent spontaneous systolic shortening is not achieved when the reperfusate has a glucose level of below 400 mg % regardless of the osmolarity of the reperfusate.

As shown in FIG. 1, % SS for reperfusion using the blood cardioplegia was positive only when both the glucose concentration and osmolarity were both over 400 mg % and 400 in Osmol, respectively. FIG. 2 is a plot of reperfusion results where the glucose concentration was kept at more than 400 mg % and the osmolarity of the cardioplegic solutions was adjusted between 380 and 480 mOsmol. As shown by FIG. 2, positive % SS was only achieved consistently when the osmolarity was greater than 400 mOsmol. FIG. 3 is a graph showing reperfusion results where glucose concentration was kept less than 400 mg % and the osmolarity of the cardioplegic solutions was varied between 380 and 480 mOsmol. As can be seen from FIG. 3, positive % SS could not be consistently achieved, regardless of the osmolarity, when the glucose concentration was below 400 mg %.

Figure 4:
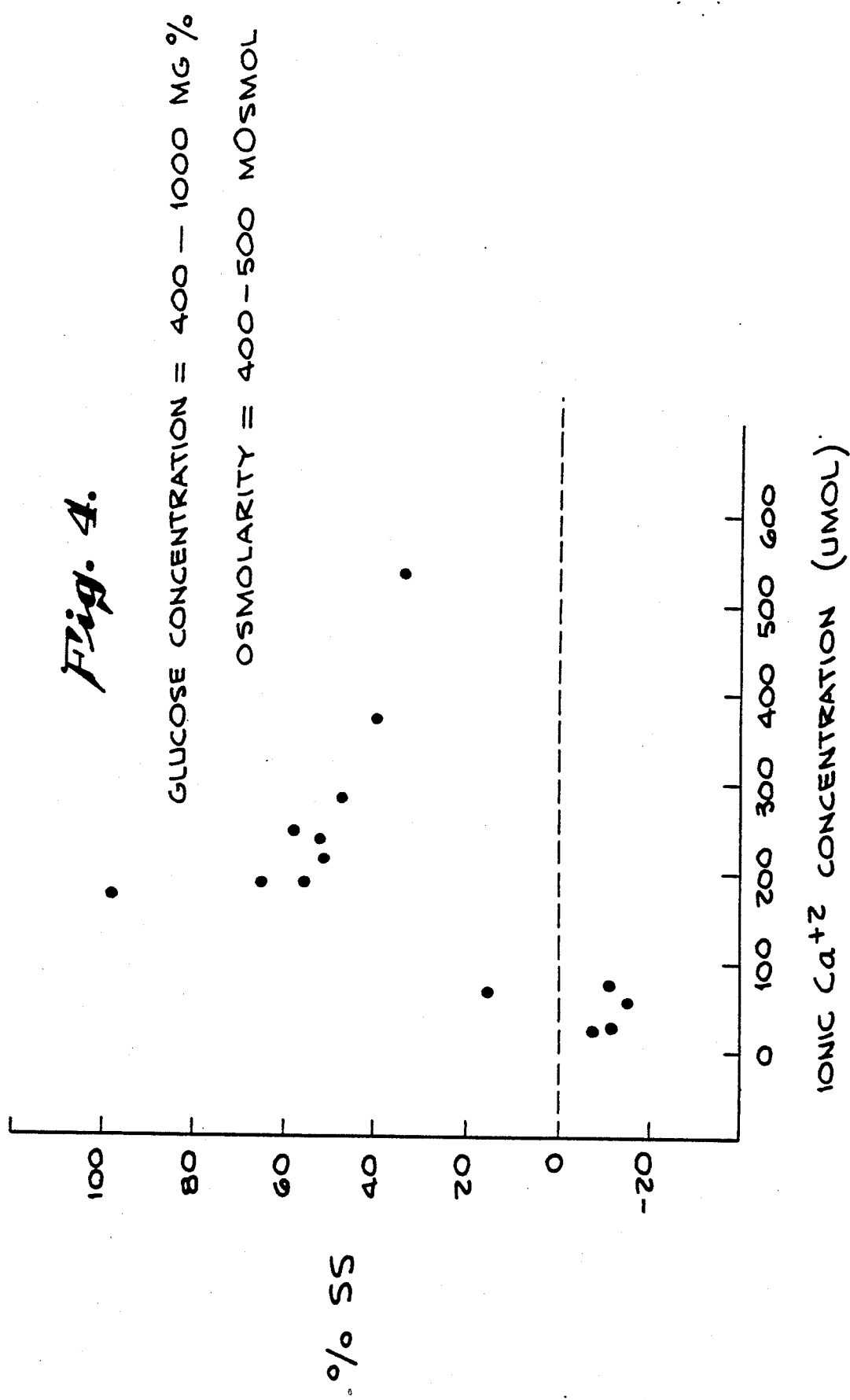
FIG. 4 is a graph representing test results which show that consistent spontaneous systolic shortening is only achieved when the ionized calcium level in the reperfusate is greater than 100 Mol.

FIG. 4 is a graph showing reperfusion results where the glucose concentration and osmolarity were maintained at values of more than 400 mg % and more than 400 mOsmol, respectively. The calcium ion concentration of the cardioplegic solution was varied between 30 umol and 500 umol. As can be seen from the graph, positive % SS was only consistently achieved when the calcium ion concentration was between 150 to 300 umol.

FIG. 5 is a graph showing myocardial damage measured for the dogs represented in FIG. 4.

Myocardial damage was estimated by vital stain technique (TTC) comparing the area of non-staining (An) to area at risk (Ar). In these studies 30% of the total left ventricular mass was at risk with regional coronary occlusion for 2 hours. Transmural biopsies were obtained from the anterior left ventricular free wall by high-speed trephine drill at the end of the reperfusion, and separated into subepicardial and subendocardial regions, and quick-frozen in liquid nitrogen. These specimens were analyzed subsequently on a Farrand Spectrofluormeter for adenine triphosphate (ATP), creatine phosphate (CP), and simultaneous biopsies were obtained to analyze tissue water content by drying them at 85° C. to a constant weight.

The area of the left ventricle at risk (Ar) was determined by re-occluding the left anterior descending coronary artery at the end of the procedure and injecting 0.25 ml/kg body weight of gentian violet dye into the left atrium. After 15 seconds, the heart was arrested with intracardiac potassium chloride, excised and trimmed of atria, great vessels, and right ventricular free wall. The remaining left ventricle was immersed in a methanol dry ice mixture to freeze the superficial layers only and cut on an electric circular slicer into 5 mm thick transverse sections. Each side of each slice was traced on acetate paper to find the stained (non-ischemic) or unstained (ischemic) tissue. The slices were then incubated in a 1% solution of Triphenyl tetrazolium chloride (TTC) for 15 minutes at 37°. The stained and non-stained areas were traced again on acetate paper. The area at risk (Ar) and area of non-staining (An) were determined by planimetry; Ar and An were expressed as percent of total left ventricular area and the ratio An/Ar was determined for each heart. As shown in FIG. 5, muscle salvage (i.e., minimum non-staining) was consistent only when the calcium ion concentration of the cardioplegic solution was between 150–300 umol.

Having thus described exemplary embodiments of the present invention, it should be noted by those skilled in the art that the within disclosures are exemplary only and that various other alternatives, adaptations and modifications may be made within the scope of the present invention. Accordingly the present invention is not limited to the specific embodiments as illustrated herein, but is only limited by the following claims.

BIBLIOGRAPHY

1. Bretschneider H. J., Hobner G., Knoll D., Lohr B., Nordbeck I. I., and Spieckermann P. G.: Myocardial resistance and tolerance to ischemia: Physiological and biochemical basis. J. Cardiovasc Surg 16, 241–260, 1975.

2. Schulte H. G., Preusse C. J., Groschopp C., Bircks W., and Bretschneider H. J.: Crstalloid cardioplegia-experience with the Bretschneider solution. Textbook of Clinical Cardioplegia, Eds Engelman & Levitsky, pp199–210, 1982.

3. Follette D. M., Mulder D. G., Maloney J. V., Buckberg G. D.: Advantages of blood cardioplegia over continuous coronary perfusion or intermittent ischemia. J Thor and Cardiovasc Surg 76(5): 604–619, 1978.

4. Lavallee M., Cox D., Patrick T. A., Vatner S. F.: Salvage of myocardial function by coronary artery reperfusion 1, 2, and 3 hours after occlusion in conscious dogs. Circulation Research 53(2):235–247, 1983.

5. Jennings R. B., Reimber K. A.: Factors involved in salvaging ischemic myocardium: effect of reperfusion of arterial blood Circ 68:I: 25–36, 1983.

6. Selinger S. L., Berg R., Leonard J. J., Coleman W. S., DeWood M. A.: Surgical intervention in acute myocardial infarction. Tx Hrt Inst J 11:1:44–51, 1984.

7. Follette D. M., Fey K., Buckberg G. D., Helly J. J., Steed D. L., Foglia R. P., Maloney J. V.: Reducing postischemic damage by temporry modification of reperfusate calcium, potassium, pH, and osmolarity. J Thor and Cardiovasc Surg 82(2):221–238, 1981.

8. Rosenkranz E. R., Buckberg, G. D.: Myocardial protection during surgical coronary reperfusion. J Am Coll Cardiol 1(5):1235–46, 1983.

9. Rosenkranz E. R., Buckberg G. D., Laks H., Mulder D. G.: Warm induction of cardioplegia with glutamate-enriched blood in coronary patients with cardiogenic shock who are dependent on inotropic drugs and intra-aortic balloon support. J. Thor and Cardiovasc Surg 86(4):507–518, 1983.

10. Rosenkranz E., Okamoto F., Vinten-Johansen J., Buckberg G., Bugyi H., Leaf J.: Advantages of aspartate-enriched glutamate blood cardioplegia in energy-depleted hearts. Abstract submitted to the AHA 56th Scientific Session, Nov. 14–17, 1983.

What is claimed is:

1. In an amino acid enriched cardioplegic solution for use in treating human hearts to prevent or reverse heart muscle damage due to ischemia, said cardioplegic solution having a calcium ion concentration, a metabolizable substrate concentration and an osmolarity, wherein the improvement comprises:

maintaining said calcium ion concentration of said cardioplegic solution at a lowered level of between about 50–300 umol;

maintaining said concentration of metabolizable substrate in said cardioplegic solution between about 400–1000 mg % wherein said metabolizable substrate is selected from the group consisting of glucose, fructose, a salt of malic acid, a salt of succinic acid and a salt of pyruvic acid; and maintaining said osmolarity of said cardioplegic solution at an increased level of between about 400–500 mOsmol.

2. An improved cardioplegic solution according to claim 1 wherein said metabolizable substrate is selected from the group consisting of glucose, fructose, malate succinate and pyruvate.

3. An improved cardioplegic solution according to claim 1 wherein said solution includes a carrier selected from the group consisting of blood, stroma free hemoglobin, oxygenated plasma and fluorocarbons.

4. An improved cardioplegic solution according to claim 3 wherein said carrier is blood.

5. An improved cardioplegic solution according to claim 2 wherein said solution includes 10–30 mmol aspartate and 10–30 mmol glutamate.

6. An improved cardioplegic solution according to claim 5 wherein said metabolizable substrate is glucose.

7. In a method for treating human hearts with an amino acid enriched cardioplegic solution to prevent or reverse heart muscle damage due to ischemia, said solution having a calcium ion concentration, a metabolizable substrate concentration and an osmolarity, wherein the improvement comprises:

maintaining said calcium ion concentration of said cardioplegic solution between about 50–300 umol;

maintaining said concentration of metabolizable substrate in said cardioplegic solution between about 400–1000 mg %; and maintaining said osmolarity of said cardioplegic solution between about 400–500 mOsmol.

8. An improved method according to claim 7 wherein said metabolizable substrate is selected from the group consisting of glucose, succinate and pyruvate.

9. An improved method according to claim 7 wherein said solution includes a carrier selected from the group consisting of blood, stroma free hemaglobin, oxygenated plasma, crystalloids and fluorocarbons.

10. An improved cardioplegic solution according to claim 9 wherein said carrier is blood.

11. An improved method according to claim 8 wherein said solution includes 10–30 mmol aspartate and 10–30 mmol glutamate.

12. An improved method according to claim 10 wherein said metabolizable substrate is glucose.

13. A composition of matter for introduction into human hearts to prevent or reverse heart muscle damage due to ischemia, said composition of matter comprising:

an aqueous solution which is adapted to be diluted with a cardioplegic compatible diluent to provide a cardioplegic solution having between about 50–300 umol calcium ion, 20–60 mmol amino acid selected from the group consisting of glutamate and aspartate, 400–1000 mg % of a metabolizable substrate and an osmolarity of between about 400–500 mOsmol.

14. A composition according to claim 13 wherein said metabolizable substrate is selected from the group consisting of glucose, fructose, a salt of malic acid, a salt of succinic acid and a salt of pyruvic acid.

15. A composition according to claim 14 wherein said metabolizable substrate is glucose.

16. A composition according to claim 13 wherein said aqueous solution is adapted to be diluted in a ratio of approximately 1 to 4 with said cardioplegic compatible diluent to provide said cardioplegic solution.

17. A composition according to claim 13 wherein said cardioplegic compatible diluent is blood.

18. An improved cardioplegic solution according to claim 1 wherein the pH of said solution is between about 7.5–7.7.

* * * * *

UNITED STATES PATENT AND TRADEMARK OFFICE
CERTIFICATE OF CORRECTION

PATENT NO. : 4,988,515
DATED : January 29, 1991
INVENTOR(S) : Gerald D. Buckberg It is certified that error appears in the above-identified patent and that said Letters Patent is hereby corrected as shown below:

In the Abstract, line 7, replace "osmolarity" with -- osmolality --.
In the Drawings, FIGS. 1, 2,3,4, and 5, replace "osmolarity" with
 -- osmolality -- (all occurrences).
Column 2, lines 12,41,46, replace "osmolarity" with
 -- osmolality -- (all occurrences).
Column 2, line 65, replace "hyperosmolarity" with
 -- hyperosmolality --.
Column 3, lines 4,9,10,28,38,65,66, replace "osmolarity" with
 -- osmolality -- (all occurrences).
Column 5, line 56, replace "osmolarity" with -- osmolality --.
Column 6, line 3, replace "osmolarities" with -- osmolalities --.
Column 7, lines 5,8,9,11,18,21, replace "osmolarity" with
 -- osmolality -- (all occurrences).
Column 8, line 60, replace "osmolarity" with -- osmolality --.
Column 9, line 3, replace "osmolarity" with -- osmolality --.

UNITED STATES PATENT AND TRADEMARK OFFICE
CERTIFICATE OF CORRECTION

PATENT NO. : 4,988,515
DATED : January 29, 1991
INVENTOR(S) : Gerald D. Buckberg It is certified that error appears in the above-identified patent and that said Letters Patent is hereby corrected as shown below:

Column 9, lines 25, 32, replace "osmolarity" with -- osmolality --
(both occurrences).
Column 10, line 21, replace "osmolarity" with -- osmolality --.

Signed and Sealed this

Thirtieth Day of January, 2001

Attest:

Q. TODD DICKINSON

*Attesting Officer*     *Director of Patents and Trademarks*

US004988515C1

(12) EX PARTE REEXAMINATION CERTIFICATE (5146th)

United States Patent
Buckberg

(10) Number: US 4,988,515 C1
(45) Certificate Issued: Jul. 19, 2005

(54) CARDIOPLEGIC SOLUTION

(75) Inventor: Gerald D. Buckberg, Los Angeles, CA (US)

(73) Assignee: Central Admixture Pharmacy Services Inc., Irvine, CA (US)

Reexamination Request:
No. 90/006,873, Nov. 20, 2003

Reexamination Certificate for:
Patent No.: 4,988,515
Issued: Jan. 29, 1991
Appl. No.: 07/333,789
Filed: Apr. 5, 1989

Certificate of Correction issued Jan. 30, 2001.

Related U.S. Application Data

(63) Continuation of application No. 07/148,151, filed on Jan. 28, 1988, now abandoned, which is a continuation of application No. 06/768,404, filed on Aug. 21, 1985, now abandoned.

(51) Int. Cl.$^7$ .................. A61K 35/14; A61K 31/70; A61K 31/195
(52) U.S. Cl. .................. 424/529; 424/682; 514/23; 514/561
(58) Field of Search ................ 424/529, 682; 514/23, 561

(56) References Cited

U.S. PATENT DOCUMENTS

| | | |
|---|---|---|
| 4,249,923 A | 2/1981 | Walda |
| 4,254,081 A | 3/1981 | Streczyn et al. |
| 4,314,550 A | 2/1982 | Apstein |
| 4,415,556 A | 11/1983 | Bretschneider |
| 4,416,280 A | 11/1983 | Carpenter et al. |
| 4,427,009 A | 1/1984 | Wells et al. |
| 4,433,971 A | 2/1984 | Lindsay et al. |

OTHER PUBLICATIONS

Bretschneider, H.J., Hobner, G., Knoll, D. Lohr, B., Nordbeck II, and Spieckermann, P.G., Myocardial Resistance and Tolerance to Ischemia, Physiological and Biochemical Basis, J. Cardiovasc Surg 16, 241–260, 1997.
Schulte, H.G., Preusse, C.J., Groschopp, C., Bircks, W., and Bretschneider solution Textbook of Clinical cardioplegia, Eds. Engelman & Levitsky, pp. 199–210, 1982.
Follette, D.M., Mulder, D.G., Maloney, J.V., Buckberg, G.D., Advantages of blood cardioplegia over continuous coronary perfusion or intermittent ischemia, J. Thor and Cardiovasc Surg 76(5), 604–619, 1978.
Lavellee, M., Cox, D., Patrick, T.A., Vatner, S.F., Salvage of myocardial function by coronary artery reperfusion 1, 2, and 3 hours after occlusion in conscious dogs, Circulation Research 53(2), 235–247, 1983.
Jennings, R. B., Reimber, K. A., Factors involved in salvaging ischemic myocardium: effect of reperfusion of arterial blood, Circ 68:I, 25–36, 1983.
Selinger, S. L., Berg, R., Leonard, J. J., Coleman, W. S., DeWood, M. A., Surgical intervention in acute myocardial infarction, Tx Hrt Inst J 11, 1:44–51, 1984.
Follette, D. M., Fey, K., Buckberg, G. D., Helly, J. J., Steed, D. L., Foglia, R. P., Maloney, J. V., Reducing postischemic damage by temporary modification of reperfusate calcium, potassium, pH, and osmolarity, J. Thor and Cardiovasc Surg 82(2), 221–238, 1981.
Rosenkranz, E. R., Buckberg, G. D., Myocardial protection during surgical coronary reperfusion, J Am Coll Cardiol 1(5), 1235–1246, 1983.
Rosenkranz, E. R., Buckberg, G. D., Laks, H., Mulder, D. G., Warm induction of cardioplegia with glutamate–enriched blood in coronary patients with cardiogenic shock who are dependent on inotropic drugs and intraaortic balloon support, J of Thor and Cardiovasc Surgery, vol. 86, No. 4, pp. 507–518, Oct. 1983.
Rosenkranz, E., Medical Research Abstract Reproduction Form from American Heart Association, Oct. 1983.
Kugelmeier, J. et al., Clinical Evaluation of Three Methods of Myocardial Protection, pp. 436–443.
Lazar, H. L., Buckberg, G. D., Manganaro, A. M., Becker, H., Myocardial energy replenishment and reversal of ischemic damage by substrate enhancement of secondary blood cardioplegia with amino acids during reperfusion, J. Thor Cardiovasc Surg 80, 350–359, 1980.
Buckberg, G. D., A Proposed "Solution" to the Cardioplegic Controversy, J. Thor Cardiovasc Surg, vol. 77, No. 6, pp. 803–815, Jun. 1979.
The Lancet, Feb. 22, 1986, G1551, pp. 397–401.
J. Thoracic and Cardiovascular Surgery, vol. 92, No. 3, Part 2 Supplement.
The Merck Index "Succinic Acid", No. 8743, p. 1271, 10th Ed. 1983.
Irisawa et al. cited in Biological Abstracts 77(10):8073, Ref. 73310, 1984.
Koomen et al., cited in Chem. Abstracts, vol. 99, No. 860424, 1983.
Gatlin L., Kulkarni P., Hussain A., DeLuca P. "Determining Osmolarities: A Practical Approach for Multicomponent Intravenous and Parenteral Nutrient Solutions." American Journal of Hospital Pharmacy. 1979, vol. 36, pp 1357–1361.
Murty B., J. Kapoor, P. DeLuca., "Compliance with USP Osmolarity Labeling Requirements" American Journal of Hospital Pharmacy. 1976, vol. 33, pp 546–551.
Huber H., W. Streng, H. Tan. "Osmolarity of Parenteral Solutions" Journal of Pharmaceutical Sciences, 1979, vol. 68 pp 1028–1032.
Streng W., H. Huber, J. Carstensen. Relationship Between Osmolality and Osmolarity: Journal of Pharmaceutical Sciences, 1978, vol. 67, pp 384–386.
Deardorff D.L. "Osmotic Strength, Osmolality, and Osmolarity". American Journal of Hospital Pharmacy, 1980, vol. 37, pp. 504–509.

(Continued)

*Primary Examiner*—Jean C. Witz

(57) ABSTRACT

An improved amino acid enriched cardioplegic solution adapted for use in preventing and treating heart muscle damage due to regional ischemia. The solution includes a calcium ion concentration of between about 50–300 umol, a metabolizable substrate concentration of 400–1000 mg % and an osmolality of between about 400–500 mOsmols.

OTHER PUBLICATIONS

H. Schott. "Osmolality/Osmolarity Data and Calculations". Pharmazie. 1979, vol. 34, pp 257–259.

Wade, D., "Domain: Body water spaces & edema". Southern Illinois University School of Medicine, 1995. http://www-.siumed.edu/mrc/working_folder/Faculty Reserves Files/Dr. Wades Stuff/ren 2.1.doc.

Hashimoto, R., "Comparison of Myocardial Protection Solutions Using a Dog Papillary Muscle Blood Perfusion Model," Nikkyo Gekaishi 32(4), 521–534. Apr. 1984.

Kito Y, Obara K, Kosakai Y, Kawazoe K, Hayashi K, Ego Y, Fujii N, Izumi B, Aono S, Naito Y, et al., "[Effects of osmolarity and oncotic pressure on myocardial protection during open heart surgery]", Kyobu Geka. 1983 Aug.;36(8):626–31.

Bercot M, Menasche P, Patris C, Tricot A, Lancrenon S, Nottin R, Viso P, Garcia A, Piwnica A, Dubost C, Mollet M. "Postoperative haemodynamic evaluation of myocardial protection by physicochemical cardioplegia Hyperkalemic, hyperosmolar and acid solution at 4 degrees C." Nouv Presse Med. Apr. 7, 1979;8(16):1327–30.

Menasche P., Kural S, Fauchet M., Lavergne A., Commin P., Bercot M., Touchot B, and Piwnica A., "Retrograde Coronary Sinus Perfusion: A Safe Alternative for Ensuring Cardioplegic Delivery in Aortic Valve Surgery," Ann Throac Surg. 1982 Dec.: 34(6): 647–58.

Menasche P., Dunica S., Kural S., Touchot B., Chollet A., Steg G., Levard G., Lorente P. and Piwnica A., "An asanguineous reperfusion solution An effective adjunct to cardioplegic protection in high–risk valve operations" J. Thorac Cardiovasc Surg 88: 278–286, Aug. 1984.

Thomas, F.T., Scnatzki, P.F., Hudson, B.H., Wolf, J.S., "Successful 24–HR Ischemic Cardiac Preservation Using A New Hyperosmolar Perfusate," Surg Forum 1975;26:253–5.

Follette, D.M., Fey, K.H., Steed, D. L., Foglia, R.P., and Buckberg, G.D, "Reducing reperfusion injury with hypocalcemic, hyperkalemic, alkalotic blood during reoxygenation." Surg.Forum 29:284–6 1978.

Rau, E., Shine K, Gervais S, Douglas A., and Amos E., Enhanced mechanical recovery of anoxic and ischemic myocardium by amino acid perfusion. Am J Physiol. 1979 Jun.;236(6):H873–9.

Follette, D., Fey, K., Mulder, D., Maloney, J., Buckberg, G.D., "Prolonged safe aortic clamping by combining membrane stabilization, multidose cardioplegia, and appropriate pH reperfusion." J. Throac. Cardiac Surg. 1977 74(5):682–694.

Pausescu, E., Mendler, N., Gebhardt, K., and Sebening, F., "Exceptional Performance in Heart Preservation with an Amino Acid–Containing Perfusion Fluid." World J. Surg. 2, 109–121, 1978.

Department of Health, Education and Welfare Grant Application HL–16292–06, Nov. 7, 1978, Surgery and Nonobstructive Coronary Insufficiency.

Department of Health, Education and Welfare Grant Application HL–16292–08, Nov. 1, 1980, Surgery and Nonobstructive Coronary Insufficiency.

Department of Health, Education and Welfare Grant Application (Supplemental) HL–16292–08S1, Feb. 1, 1980, Surgery and Nonobstructive Coronary Insufficiency.

Department of Health, Education and Welfare Grant Application HL–16292–09, Jan. 11, 1982, Surgery and Nonobstructive Coronary Insufficiency.

Department of Health, Education and Welfare Grant Application HL–16292–10, Dec. 15, 1982, Surgery and Nonobstructive Coronary Insufficiency.

Defendant's Memorandum on Claim Construction, Aug. 20, 2001.

Defendants' Response to Plaintiff's Proposed Claim Construction, Sep. 14, 2001.

Defendant's Supplemental Brief On Claim Construction, Jan. 28, 2002.

Plaintiff Central Admixture Pharmacy Services, Inc.'s Proposed Claim Construction, Aug. 20, 2001.

Plaintiff's Response Brief on Claim Construction, Sep. 14, 2001.

Plaintiff's Supplemental Brief on Claim Construction, Jan. 28, 2002.

Transcript Markman Hearing, U.S. District Court for the Northern District of Alabama, Apr. 30, 2001.

Order, United States District Court for the Northern District of Alabama, entered, May 2, 2002.

Order, United States District Court for the Northern District of Alabama, entered, Sep. 4, 2003.

Complaint For Patent Infringement, Filed Aug. 31, 2000.

Answer And Counterclaim, Served Oct. 2, 2000.

Amended Answer And Counterclaim, Served Nov. 29, 2000.

Answer to Amended Counterclaim, Served Jan. 3, 2001.

CAPS' Proposed Claim Construction; Declaration of P. Afrasiabi Filed Concurrently Herewith, Filed Aug. 20, 2001.

Defendants' Memorandum On Claim Construction, Served Aug. 20, 2001.

Defendants' Evidentiary Submission in Support of Their Memorandum on Claim Construction, Served Aug. 20, 2001.

Order Re Oral Argument on Plantiff's Motion for Partial Summary Judgment on Defendants' Counterclaims II and III and on the Claim Construction Issues (Rescheduled To Oct. 30, 2001 At 9:30 A.M.), Filed/Entered Sep. 6, 2001.

Plaintiff's Response Brief on Claim Construction, Served Sep. 14, 2001; Supplemental Declaration of Peter R. Afrasiabi Filed with CAPS Response to Defendants' Memorandum on Claim Construction And Declaration Of Stanley Bruce Digerness, Dated Sep. 6, 2001.

Declaration of Dr. Stanley Bruce Digerness, Dated Sep. 14, 2001.

Defendants' Response to Plaintiffs Proposed Claim Construction, Served Sep. 14, 2001.

Report of Dr. Robert M. Riggs, Served Dec. 10, 2001.

Expert Witness Report of Hal Patterson, Served Dec. 10, 2001.

Expert Witness Report of Dr. Stanley Digerness, Served Dec. 10, 2001.

Expert Witness Report Of William L. Holman, M.D., Served Dec. 10, 2001.

First Supplemental Expert Witness Report of Dr. Stanley Digerness, Served Jan. 22, 2002.

First Supplemental Expert Witness Report of William L. Holman, M.D., Served Jan. 22, 2002.

Defendant's Rule 26(A)(2) Expert Response Report of Dr. David R. Wade, Served Jan. 22, 2002.

Defendant's Supplemental Brief On Claim Construction, Served Jan. 28, 2002.

Defendants' Evidence Submitted in Support of Their Supplemental Brief of Claim Construction, Served Jan. 28, 2002.

Plaintiff's Supplemental Brief on Claim Construction, Served Jan. 28, 2002.
Supplemental Declaration of Dr. Stanley Bruce Digerness, Served Jan. 28, 2002.
Second Supplemental Expert Witness Report of William L. Holman, M.D., Served Feb. 11, 2002.
Plaintiff's Supplemental Brief on Southwest Software, Served Feb. 22, 2002.
Defendant's Responsive Brief Regarding the Effect of the Phrase "Causes Thereafter Arising" In 35 U.S.C. § 255 on the Validity of the Certificate of Correction and Its Application to Plaintiff's Claims, Served Feb. 27, 2002.
Notice of Filing Joint Claim Construction Chart, Served Apr. 23, 2002.
Order Re: Markman Hearing, Entered May 2, 2002.
Defendant's Motion to Reconsider Markman Claim Construction, Served May 13, 2002.
Defendant's Memorandum in Support of Its Motion to Reconsider the Court's Markman Claim Construction, Served May 13, 2002.
Proposed Claim Chart in Accordance with the Court's May 2, 2002 Order, Filed May 15, 2002.
Defendants' Objection to the Proposed Claim Chart in Accordance with the Court's May 2, 2002 Order, Served May 16, 2002.
Plaintiff's Opposition to Defendants' Motion to Reconsider Markman Claim Construction, Filed May 30, 2002.
Defendant's Validity Report of Dr. Robert M. Riggs, Served Jun. 7, 2002.
Defendants's Reply to Plaintiff's Opposition to Motion to Reconsider the Court's Markman Claim Construction, Served Jun. 10, 2002.
Order Re Plaintiff's Motion for Partial Summary Judgment, Entered Sep. 4, 2003.
Order Re Defendant's Motion to Reconsider Markman Claim Construction, Entered Sep. 4, 2003.
Defendants' Further Objection to the Claim Chart in View of the Court's Order Of Sep. 4, 2003, Served Sep. 9, 2003.
Plaintiff Central Admixture Pharmacy Services, Inc.'s Motion for Summary Judgment No. 2: No Validity of U.S. Pat. No. 4,988,515, Filed Nov. 21, 2003.
Responsive Expert Witness Report of William L. Holman, M.D., Dated Nov. 21, 2003.
Defendants' Rebuttal Report to Perfusion Procedures During Cardiac Surgery, Dated Nov. 21, 2003.
Request for Ex Parte Reexamination and Transmittal Form, Dated Nov. 20, 2003.
Defendants' Response to Plaintiff's Motion for Summary Judgment on Invalidity [Exhibits Are In Exhibit Clip 10], Dated Jan. 14, 2004.
Defendants' Supplemental Response to Plaintiff's Motion for Summary Judgment on Invalidity and Declaration of Brendan E. Squire, Dated Jan. 27, 2004.
USPTO Decision Granting the Request for Ex Parte Reexamination, Dated Feb. 12, 2004.
Defendants' Motion for Stay Pending Reexamination, Dated Feb. 19, 2004.
Order to Show Cause (Re Defendants' Motion for Stay Pending Re-Exam), Dated Feb. 24, 2004.
37 C.F.R. § 1.530 Response to Order Granting Request for Ex Parte Reexamination, Dated Mar. 2, 2004.
Defendant's Response to Plaintiff's Showing, Dated Mar. 3, 2004.
Plaintiff's Response to Order to Show Cause and Opposition to Defendants' Motion to Stay Pending Re-Examination, Dated Mar. 1, 2004.
Defendants' Supplemental Motion on Claim Construction and "Causes Thereafter Arising"; Memorandum in Support, Dated Mar. 23, 2004.
Plaintiff CAP's Opposition to Defendants' Motion for Summary Judgment of Invalidity, Dated Apr. 13, 2004.
Plaintiff CAPS's Opposition to and Motion to Strike Defendants' Supplemental Motion on Claim Construction and "Causes Thereafter Arising," Dated Apr. 13, 2004.
Second Supplemental Appendix of Exhibits in Support of CAP's Oppositions to Defendants' MSJ of Invalidity, Opposition to Defendants' MSJ of No Infringement, Opposition to and Motion to Strike Defendants' Supplemental Motion on Claim Construction and "Causes Thereafter Arising," and Opposition to Defendants' Motion to Dismiss Defendant Charles Wall, Dated Apr. 13, 2004.
Declaration of Nathaniel L. Dilger in Support of #150, Dated Apr. 13, 2004.
Plaintiff's Response to Defendants' Statement of Facts in Opposition to Defendants' Motions for Summary Judgment, Dated Apr. 13, 2004.
Defendants' Reply to Plaintiff's Response to Defendants' Motion for Summary Judgment of Invalidity, Dated Apr. 27, 2004.
37 C.F.R. 1.535 Reply By Third Party Requester in Ex Parte Reexamination, Dated Apr. 30, 2004.
Plaintiff's Opposition to Defendants' Motion to Grant Access to U.S. Appl. No. 07/613,120, Dated May 11, 2004.
Defendants' Reply to Plaintiff's Opposition to Defendant's Motion to Grant Access to U.S. Appl. No. 07/613,120, Dated May 20, 2004.
Motion In Limine [Exhibits Are In Exhibit Clip 15, vol. 11], Dated Jun. 7, 2004.
Defendants' Motion In Limine to Exclude the Test Results of Hal Patterson, Dated Jul. 1, 2004.
Defendant's Reply to Plaintiff's Opposition to Defendants' Motion In Limine to Exclude the Test Results of Hal Patterson, Dated Jul. 13, 2004.
Motion for Leave to File Supplemental Materials and Arguments Regarding Defendants' Motion for Summary Judgment of Invalidity and a New Motion for Judgment of Non-Enforceability Due to Inequitable Conduct By the Patentee In Procurement of U.S. Pat. No. 4,988,515, Dated Aug. 31, 2004.
Defendants' Motions for Summary Judgment on Common Law Fraud and Inequitable Conduct In Procurement of U.S. Pat. No. 4,988,515 And Alternatively, for Leave to Take the Deposition of Gerald Buckberg Regarding Matters Objeted to During His Deposition as a Non-Party Witness and to Take the Deposition of David Oldenkamp, Dated Aug. 31, 2004.
Defendants' Memorandum In Support of Motions for Summary Judgment on Common Law Fraud and Inequitable Conduct In Procurement of U.S. Pat. No. 4,988,515 And Motions for Leave to Take the Deposition of Gerald Buckberg Regarding Matters Objected to During His Deposition as a Non-Party Witness and to Take the Deposition of David Oldenkamp, Dated Aug. 13, 2004.
Defendants' Supplemental Memorandum In Support of Motions for Summary Judgment of Invalidity, Dated Aug. 31, 2004.

Defendant's Evidentiary Submission in Support of Defendants' Motions for Summary Judgment on Common Law Fraud and Inequitable Conduct In Procurement of U.S. Pat. No. 4,988,515 And Motions for Leave to Take the Deposition of Gerald Buckberg Regarding Matters Objected to During His Deposition as a Non–Party Witness and to Take the Deposition of David Oldenkamp And Defendants' Supplemental Memorandum in Support of Motions for Summary Judgment of Invalidity, Dated Aug. 31, 2004.

Transcript of Deposition of Hal Patterson, dated Jan. 4, 2004 in Case No. CV–00–HS–2430–S (formerly CV 00–B–2430–S), with exhibits.

Transcript of Deposition of William Holman, M.D. dated Jan. 6, 2004 in Case No. CV–00–HS–2430–S (formerly CV 00–B–2430–S), with exhibits.

Transcript of Deposition of Dr. Stan Digerness dated Jan. 7, 2004 in Case No. CV–00–HS–2430–S (formerly CV 00–B–2430–S), with exhibits.

Transcript of Deposition of Dr. Robert M. Riggs dated Jan. 8, 2004 in Case No. CV–00–HS–2430–S (formerly CV 00–B–2430–S), with exhibits.

Transcript of Deposition of Dr. David R. Wade dated Jan. 9, 2004 in Case No. CV–00–HS–2430–S (formerly CV 00–B–2430–S), with exhibits.

Transcript of Deposition of Dr. Stanley Bruce Digerness dated Jan. 26, 2004 in Case No. CV–00–HS–2430–S (formerly CV 00–B–2430–S), with exhibits.

Application for Continuation Grant, Grant #HL 16292–07, Department of Health, Education and Welfare Public Health Service, Nov. 1, 1979, cover page, pp. 6–8.

Buckberg, Letter to Raymond J. Lipicky, Department of Health and Human Services Food and Drug Administration, May 30, 1985, 6 pages.

Buckberg, Letter to Secretary of Health, Education and Welfare Commisioner of Food and Drugs, Aug. 27, 1984, 10 pages.

Buckberg, et al., "Techniques for Administering Clinical Cardioplegia—Blood Cardioplegia," *Textbook of Clinical Cardioplegia*, 1982, Chapter 22, pp. 305–316, Futura Publishing Company.

Dyson, et al., "A Hemodilution Cardioplegia and a Proposed Delivery System," *The Journal of Extra–Corporeal Technology*, 1980, vol. 12, No. 4, pp. 86–88.

Engelman, et al., *A Textbook of Clinical Carioplegia*, 1982, Futura Publishing Company, 7 pages.

Henry, "Clinical Diagnosis and Management," *Laboratory Methods, 17th Edition*, W. B. Saunders Company, 1984, cover page, pp. 37, 38, 394, 1024, 1025, 1432–1437.

Koch–Weser, "Influence of Osmolarity of Perfusate on Contractility of Mammalian Myocardium," *American Journal of Physiology*, The American Physiological Society, Jun. 1963, vol. 204, No. 6, cover page, pp. 957–962.

New Drug Application, submitted 1984–1985, File No. F03–14864, (Bates Nos. ACS004837–ACS004925) 89 pages.

Rocks, et al., "Whole Blood Osmolality," *Ann. Clin. Biochem*, 1986, vol. 23, pp. 106–108.

Weil, et al., "Measurement of Whole Blood Osmolality," *American Society of Clinical Pathologists*, Apr. 1982, pp. 447–448.

Wildenthal, "Effects of Hyperosmolality on Cardiac Muscle Mechanics in Vivo and in Vitro," *Proceedings of the Physicological Society*, Apr. 1969, pp. 50p–51p.

Winbury, "Influence of Glucose on Contractile Activity of Papillary Muscle During and After Anoxia," *Effects of Glucose on Anoxia*, pp. 135–138.

Wyte, "Cardioplegic Solution: What Combination of Additives?," *Pathophysiology and Techniques of Cardiopulmonary Bypass*, Williams & Wilkins, London, 1983, vol. II, Chapter 13, cover page 2 pages, pp. 138–151.

The Following Documents Were Filed in Litigation Involving U.S. Pat. No. 4,988,515, Currently Pending in the U.S. District Court for the Northern District of Alabama, Southern Division, Case No. CV–00–HS–2430–S (Formerly CV 00–BE–2430–S).

Reply In Support of Plaintiff's Motion for Summary Judgment No. 2: No Invalidity of U.S. Pat. No. 4,988,515, dated Feb. 13, 2004, 29 pages.

Plaintiff's Objections to Evidence Submitted by Defendants In Opposition to Plaintiff's Motion for Summary Judgment, dated Feb. 13, 2004, 5 pages.

Reply Declaration of William L. Holman, M.D., In Support of CAPS' Motions for Summary Judgment, dated Feb. 13, 2004, 8 pages.

Supplemental Appendix of Exhibits In Support of CAPS' Motions for Summary Judgment; Declaration of Dilger In Support of CAPS' Reply Motions for Summary Judgment Nos. 1, 2, and 3, dated Feb. 13, 2004, 95 pages.

Defendants' Motion for Summary Judgment of Invalidity; Memo In Support, dated Mar. 23, 2004, 29 pages.

Motion to Grant Access to U.S. Appl. No. 07/613,120, dated Apr. 20, 2004, 142 pages.

Defendants' Response to Plaintiff's Statement of Facts Regarding Invalidity, dated Apr. 27, 2004, 18 pages.

Defendants' Reply to Plaintiff's Opposition to and Motion to Strike Defendants' Supplemental Motion on Claim Construction and "Causes Thereafter Arising", dated Apr. 27, 2004, 11 pages.

Defendants' Supplemental Exhibits In Reply to Plaintiff's Response to Defendants' Motion for Summary Judgment, dated Apr. 27, 2004, 158 pages.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *